United States Patent
Weichselbaum et al.

(10) Patent No.: US 7,331,923 B2
(45) Date of Patent: Feb. 19, 2008

(54) INSEMINATION DEVICE

(75) Inventors: Amnon Weichselbaum, Haifa (IL); Shalom Bar-Ami, Haifa (IL); Ronnie Klein, Haifa (IL)

(73) Assignee: Fertiligent Ltd., Migdal HaEmek (IL)

( * ) Notice: Subject to any disclaimer, the term of this patent is extended or adjusted under 35 U.S.C. 154(b) by 402 days.

(21) Appl. No.: 11/084,139

(22) Filed: Mar. 21, 2005

(65) Prior Publication Data

US 2005/0165270 A1     Jul. 28, 2005

Related U.S. Application Data

(63) Continuation-in-part of application No. PCT/IL03/00750, filed on Sep. 17, 2003.

(60) Provisional application No. 60/411,757, filed on Sep. 19, 2002.

(51) Int. Cl.
  *A61B 17/43* (2006.01)
(52) U.S. Cl. .................................................. 600/35
(58) Field of Classification Search ............ 600/33–35; 222/628, 189.08, 630–633, 460, 461, 498, 222/499
  See application file for complete search history.

(56) References Cited

U.S. PATENT DOCUMENTS

| 5,562,654 | A | 10/1996 | Smith | |
| 5,904,665 | A | 5/1999 | Muharib | |
| 5,976,389 | A * | 11/1999 | Zavos | 210/807 |
| 6,129,214 | A | 10/2000 | Bar-Ami et al. | |
| 6,357,596 | B1 | 3/2002 | Weichselbaum et al. | |
| 2003/0038087 | A1 * | 2/2003 | Garvin | 210/767 |
| 2003/0189003 | A1 * | 10/2003 | Kraus et al. | 210/649 |
| 2005/0032097 | A1 * | 2/2005 | Garvin | 435/6 |

FOREIGN PATENT DOCUMENTS

| FR | 2614899 | 11/1988 |
| WO | WO 82 00754 | 3/1982 |
| WO | WO 96 18350 | 6/1996 |
| WO | WO 01 17443 | 3/2001 |

\* cited by examiner

*Primary Examiner*—Samuel G. Gilbert
(74) *Attorney, Agent, or Firm*—Dekel Patent Ltd.; David Klein

(57) ABSTRACT

An insemination device including a sperm reservoir including sperm therein, a pump in fluid communication with the sperm reservoir and operative to pump sperm therefrom, and a filter in fluid communication with the pump adapted to filter the sperm to form a sperm filtrate that has a higher fertility potential than the sperm before being filtered by the filter, wherein the filter includes a multi-layer membrane for sperm filtration, including at least one first layer with a shape and pore size for preliminary filtration of relatively large particles and at least one second layer with a shape and pore size for filtration of relatively smaller particles.

9 Claims, 1 Drawing Sheet

INSEMINATION DEVICE

CROSS REFERENCE TO OTHER APPLICATIONS

This application is a continuation-in-part of PCT application PCT/IL2003/000750, filed Sep. 17, 2003, published Apr. 1, 2004 as WO 2004/026154, which claims priority from U.S. provisional patent application 60/411,757, filed 19 Sep. 2002, and from U.S. patent application Ser. No. 10/600,331, now abandoned.

FIELD OF THE INVENTION

The present invention relates generally to methods and apparatus for insemination, and particularly to methods and devices for slow-release insemination with filtration.

BACKGROUND OF THE INVENTION

Artificial insemination is commonly used to increase pregnancy rates and overcome fertility problems for humans and is also often used to breed animals by using semen from males with desirable genetics. While many methods and devices are known for achieving artificial insemination, it is believed that many of the known techniques are inconvenient, expensive and have been less than successful in achieving higher pregnancy rates.

For example, in humans, artificial insemination is often accomplished by using the intrauterine insemination or cervical insemination in which semen is directly deposited into the uterus or the cervix, respectively, using a pipette. Another technique is cup insemination, in which a cervical cup is filled with 0.5-1 ml. of semen and placed over the patient's cervix.

Each of the above mentioned methods has its shortcomings. Cervical insemination may correlate with only about 10% of pregnancy rates. One reason may be a hostile cervical canal due to various factors such as viscous mucus, acidic mucus, infections, and sperm antibodies. Another reason may be a significant loss of semen that flows down to the vagina.

Intrauterine insemination does not offer significant advantage in pregnancy results as compared to cervical insemination (10%) and its main shortcoming is the loss of material to the cervix and vagina.

Various patents have proposed solutions for artificial insemination. U.S. Pat. No. 6,551,236 to Liegois describes an artificial insemination device for breeding animals, such as sows, including a catheter suitable for being introduced into the genital system so as to enable sperm to be discharged therefrom and a reservoir of sperm connected to the catheter. The catheter has a conduit with an end piece at a distal end thereof. The conduit is suitable for lodging in the neck of the animal's uterus. A ring is provided so as to form a tight seal between the reservoir and the catheter.

U.S. Pat. No. 6,511,415 to Christine, et al. describes an apparatus for artificial insemination of mammals. An apparatus for depositing media into the uterus of a mammal includes a conical chamber that has a plurality of perforations and flaps. An exterior spiral formation is configured for traversing or penetrating cervical passageway. A sheath having a frusto-conical rearward end extends axially from an aft end of the conical chamber. A tubular depositing chamber extends axially from the conical chamber to a position beyond a fore end of the conical chamber. Coupled to the rearward end of the depositing chamber is an embryo or semen packaging unit. The tubular depositing chamber has an end that has an aperture to permit the flow of semen out of the depositing chamber and into the uterus.

U.S. Pat. No. 6,004,260 to Thompson describes an apparatus and method for the application of spermatozoa to the intrauterine cavity of a female. In this patent, a first pressurizable chamber is introduced within an intrauterine cavity of a female. A second pressurizable chamber is introduced outwardly of the first pressurizable chamber. The first pressurizable chamber is filled with spermatozoa, and the outer (second) pressurizable chamber is filled with a pressurizable fluid, so as to affect discharge of the spermatozoa from the innermost first pressurizable chamber over an extended period of time.

U.S. Pat. No. 5,904,665 to Nabil Muharib, describes a method for automated, prolonged slow-release, artificial intrauterine insemination. Motile sperm is introduced into the uterus in a programmed, organized and metered pattern over an extended period of time. A catheter is inserted into the uterine cavity and aliquots of sperm containing medium are injected at a rate of 10 to 20 mm/hr (approximately every 30 seconds) for between 4 to 6 hours. The motile sperm content of each aliquot is between 8,000 and 75,000.

A device is provided that comprises a flexible catheter having a delivery channel, a first end attachable to a pumping means, and a second end (uterine end) adapted to pass through the cervix and into the uterine cavity. The catheter is provided with an inflatable balloon adjacent the second end. Upon inflation of the balloon, the catheter is immobilized in the vagina. The pumping means delivers the aliquots of sperm containing medium through the delivery channel and into the uterus. The balloon is deflatable to permit the catheter's easy removal after use.

U.S. Pat. No. 5,562,654 to Todd Smith describes an apparatus for the time-released delivery of a selected preparation into a patient's uterine cavity. The apparatus includes an osmotic pump for expelling the selected preparation over time and a catheter for delivery the expelled preparation into the uterine cavity. An inflatable balloon on the catheter holds the apparatus in position in the patient (like U.S. Pat. No. 5,904,665).

U.S. Pat. No. 5,536,243 to Jeyendran describes a self-contained time-release artificial insemination device that introduces a bolus of semen into the cervical canal or uterus over a period of hours. The device includes a cervical cap adapted to conform and adhere to the cervix and includes an elongated nipple that extends in a perpendicular direction from the cap for insertion into the cervical canal or uterus. A time-release mechanism is provided in communication with the nipple for delivering semen through the nipple.

SUMMARY OF THE INVENTION

The present invention seeks to provide an innovative slow-release insemination device, which enables in-vivo, real time sperm improvement, as described more in detail hereinbelow. The present invention may minimize loss of sperm by slow-release of fluid. The sperm may be injected directly into the uterus of a female, avoiding the cervical hostile environment. The female may be free to ambulate within 4-6 hours of injection, minimizing discomfort.

The process of controlled slow-release of the sperm into the uterus and the use of a selective filter may enable release of only motile sperm. By lengthening the period of "window of opportunity" for ovum fertilization, it may be possible to increase pregnancy rates after artificial insemination.

There is thus provided in accordance with an embodiment of the present invention an insemination device comprising a sperm reservoir comprising sperm therein, a pump in fluid communication with the sperm reservoir and operative to pump sperm therefrom, and a filter in fluid communication with the pump adapted to filter the sperm to form a sperm filtrate that has a higher fertility potential than the sperm before being filtered by the filter. The filter may be in fluid communication with an outlet or inlet of the pump.

In accordance with an embodiment of the present invention a catheter is in fluid communication with the filter downstream of the pump. The catheter may comprise a hysterosalpingography (HSG) catheter that includes a fixing balloon.

Further in accordance with an embodiment of the present invention a controller is in operative communication with the pump, adapted to control operation of the pump.

BRIEF DESCRIPTION OF DRAWINGS

The present invention will be further understood and appreciated from the following detailed description taken in conjunction with the drawings in which.

DETAILED DESCRIPTION OF THE INVENTION

Figure 1:
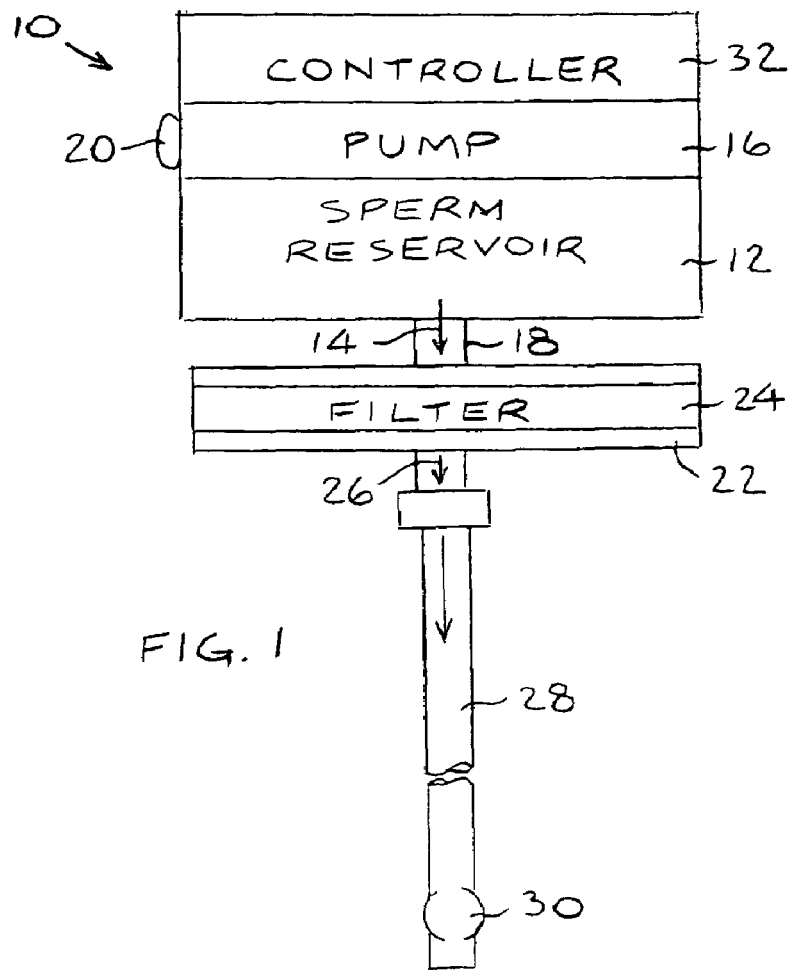
FIG. 1 is a simplified illustration of an insemination device, constructed and operative in accordance with an embodiment of the invention.

Reference is now made to FIG. 1, which illustrates an insemination device 10, constructed and operative in accordance with an embodiment of the invention.

Insemination device 10 may comprise a sperm reservoir 12 comprising sperm 14 therein. Sperm 14 (also referred to as semen) may typically comprise materials such as viable spermatozoa, paternal plasma, RCM (residual cytoplasmic masses) that secrete ROS (Reactive Oxygen Species), proteins, hormones (such as prostaglandins), leukocytes and other round cells, and dead, agglutinated or nonviable spermatozoa. The nonviable materials may interfere with successful fertilization and with the successful maintenance of a fertilized ovum in the female patient. Moreover, seminal plasma may cause severe uterine cramping, and worse, may result in spontaneous abortion of the fertilized ovum. Sperm reservoir may hold any suitable volume of sperm 14, such as but not limited to, about 0.3-1.5 cc.

A pump 16 may be in fluid communication with sperm reservoir 12. Pump 14 may comprise, without limitation, a diaphragm pump, a peristaltic pump, or an electromechanical pump, among others. For example, in one embodiment of the invention, pump 16 may comprise a miniature pump with sperm reservoir 12 being bounded by two diaphragms. Pump 16 is preferably disposable and made of medical grade sperm compatible plastics. Pump 16 may include an inner gas generator that pushes the sperm contained between the two inner diaphragms out of a pump outlet 18. Pump 16 may be, but is not limited to, a size of about 5 cm long, 4 cm wide and 2 cm thick, and may be adhered to a portion of a patient's body, such as but not limited to, the groin. However, the invention is not limited to this size, and in general, pump 16 may be external to the body or internal, e.g., small enough to pass into or through the vagina. Pump 16 may have an operation button 20.

Pump 16 may pump sperm 14 via outlet 18 to a filter housing 22. Pump 16 may be connected to filter housing 22 by means of, but not limited to, a standard Luer lock adaptor. Filter housing 22 may have, but is not limited to, a disc like shape. Filter housing 22 comprises therein a filter 24, which is adapted to filter sperm 14 to form a sperm filtrate 26 that has a higher fertility potential than the non-filtered sperm 14.

Filter 24 may comprise, without limitation, a nylon filter with a pore size under 8 microns, e.g., 3-8 microns. Non-human sperm samples may require different pore sizes. The invention is not limited to nylon mesh, and other mesh materials may be used. One purpose of filter 24 is to ensure that throughout the slow insemination only the motile sperm are capable for active penetration (by "drilling") of the filter's pores, while "round cells" (which are, for example, greater than 8 microns in diameter) and immotile, agglutinated or nonviable spermatozoa may not pass through filter 24, thereby preventing them from secreting their harmful chemicals in the uterus and fertilization site. A finer pore size may also be used and yield even a higher quality sperm filtrate 26, but may reduce the amount of sperm filtrate 26. Conversely, a greater pore size may also be used and yield a larger amount of sperm filtrate 26, but with a lower quality, i.e., less motile sperm. Of course, the higher percent quality of the sperm filtrate 26, the greater the likelihood of achieving fertilization.

It is noted that insemination device 10 with filter 24 is different from the sperm strainer system described in U.S. Pat. No. 6,129,214 to Bar-Ami and Weichselbaum. Filter 24 of the present invention may preferably comprise a multilayer membrane for sperm filtration, in contrast to the filter of U.S. Pat. No. 6,129,214, which includes only one membrane. The first layer or set of layers of the filter membrane of filter 24 have a specific shape and pore size for preliminary filtration of larger particles (e.g., greater than 5 microns in diameter). The second layer or set of layers of the filter membrane of filter 24 have a specific shape and pore size (e.g., 3-5 micron pore size) for specifically passing the motile sperm and preventing the non-motile sperm (and other somatic cells and particles) from passing through. It has been found that one filter (such as in U.S. Pat. No. 6,129,214) gets clogged with white blood cells and other debris and does not successfully enable the motile sperm to pass through the filter.

Minimal force is needed in order to ensure contact between the sperm 14 and filter 24. The natural, self-actuated migration of the more motile sperm in sperm reservoir 12 may assure that the sperm that do encounter and work their way through filter 24 may have a significantly higher motility index than the remaining sperm. Moreover, the less motile sperms and the dead sperms are accumulated in the lower portion of the semen sample while the motile sperm move (against gravity force) to the upper portion of the semen sample to contact and penetrate filter 24. The present invention's ability to work against gravity is not found in the prior art.

In the illustrated embodiment, filter 24 is in fluid communication with outlet 18 of pump 16. A catheter 28 may be in fluid communication with filter 24 downstream of pump 16. Catheter 28 may comprise, without limitation, a hysterosalpingography (HSG) catheter that includes a fixing balloon 30 (e.g., with up to 3 cc volume). For example, catheter may be about 280 mm in length with an upper orifice and may be 5 F (1F=0.3 mm) in diameter. The invention is not limited to this example. Such catheters are readily available from a variety of manufacturers, such as Cook Urological and Marina Medical. The entire insemination device 10 may be supplied as one unit in a sterilized package.

Catheter 28 may pass through the cervix and into the uterus (not shown) to deliver the sperm filtrate 26 to the fertilization site.

Insemination device 10 may comprise a controller 32, which may control operation and timing of pump 16. For example, the insemination may be a slow-release insemination, wherein the sperm filtrate 26 is delivered to the fertilization site over 4-6 hours, although the invention is not limited to this range.

Figure 2:
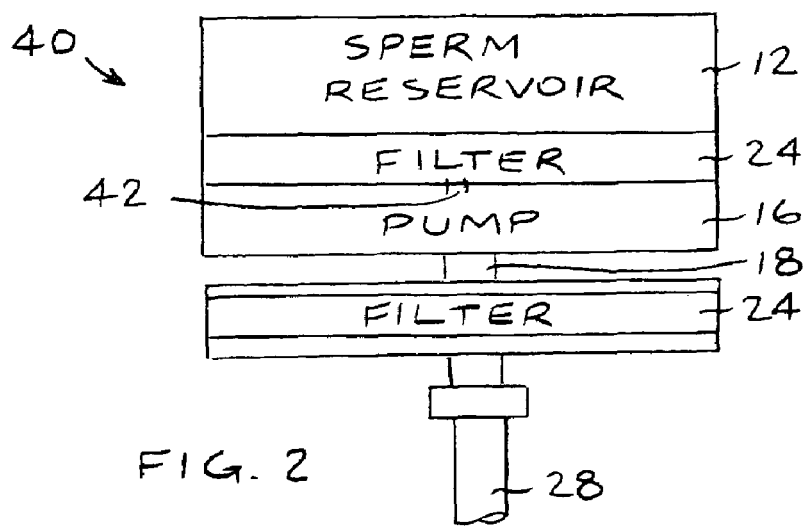
FIG. 2 is a simplified illustration of an insemination device, constructed and operative in accordance with another embodiment of the invention.

Reference is now made to FIG. 2, which illustrates a variation of insemination device 10, called insemination device 40, constructed and operative in accordance with another embodiment of the invention. In this variation, filter 24 may be in fluid communication with an inlet 42 of pump 16, wherein the sperm is pre-filtered before entering pump 16. Another filter 24 may be provided downstream of pump 16, as in the embodiment of FIG. 1.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. An insemination device comprising:
a sperm reservoir comprising sperm therein;
a pump in fluid communication with said sperm reservoir and operative to pump sperm therefrom; and
a filter in fluid communication with said pump adapted to filter said sperm to form a sperm filtrate that has a higher fertility potential than said sperm before being filtered by said filter, wherein said filter comprises a multi-layer membrane for sperm filtration, comprising at least one first layer with a shape and pore size for preliminary filtration of first particles and at least one second layer with a shape and pore size for filtration of second particles relatively smaller than the first particles, wherein said at least one second layer has a 3-5 micron pore size.

2. The insemination device according to claim 1, wherein said at least one first layer has a shape and pore size for preliminary filtration of particles greater than 5 microns in diameter.

3. The insemination device according to claim 1, wherein said filter is in fluid communication with an outlet of said pump.

4. The insemination device according to claim 1, further comprising a catheter in fluid communication with said filter downstream of said pump.

5. The insemination device according to claim 4, wherein said catheter comprises a hysterosalpingography (HSG) catheter that includes a fixing balloon.

6. The insemination device according to claim 1, wherein said filter is in fluid communication with an inlet of said pump.

7. The insemination device according to claim 6, further comprising a catheter in fluid communication with said filter downstream of said pump.

8. The insemination device according to claim 7, wherein said catheter comprises a hysterosalpingography (HSG) catheter that includes a fixing balloon.

9. The insemination device according to claim 1, further comprising a controller in operative communication with said pump, adapted to control operation of said pump.

\* \* \* \* \*